United States Patent [19]
Smith

[11] Patent Number: 5,595,570
[45] Date of Patent: Jan. 21, 1997

[54] KERATOME WITH SPRING LOADED ADJUSTABLE PLATE, CUTTING LENGTH ADJUSTMENT PLATE, METHOD OF CUTTING A CORNEAL FLAP, AND GAUGE-MOUNTED BRACKET FOR ADJUSTING PLATE ON KERATOME HEAD

[75] Inventor: G. Richard Smith, Fountain Hills, Ariz.

[73] Assignee: S.C.M.D., Ltd., Fountain Hills, Ariz.

[21] Appl. No.: 349,782

[22] Filed: Dec. 6, 1994

[51] Int. Cl.⁶ .................................................. A61B 17/00
[52] U.S. Cl. ............................................................ 606/166
[58] Field of Search ................................. 606/166, 167; 128/753, 754

[56] References Cited

U.S. PATENT DOCUMENTS 4,662,370  5/1987  Hoffmann et al. ...................... 606/166
5,133,726  7/1992  Ruiz et al. ............................... 606/166
5,496,339  3/1996  Koepnick ................................. 606/166

Primary Examiner—Michael Powell Buiz
Assistant Examiner—William Lewis
Attorney, Agent, or Firm—Meschkow & Gresham P.L.C.

[57] ABSTRACT

A cutting length adjustment plate for a keratome that allows for a pre-cutting measurement of a corneal cut has a transverse groove adapted to receive a keratome, a parallel aperture in the groove for viewing the blade in the keratome, and indicia to measure the distance of the tip of the blade to the rear end of the keratome. A method of cutting a sized corneal flap is also disclosed. The invention further comprises a keratome with a spring loaded adjustable plate having a groove in which to retain a free end the spring. A collar to support the spring is also present. Lastly, a bracket is disclosed for use in measuring and adjusting the cutting depth of the keratome. The method for using the bracket is also disclosed.

6 Claims, 2 Drawing Sheets

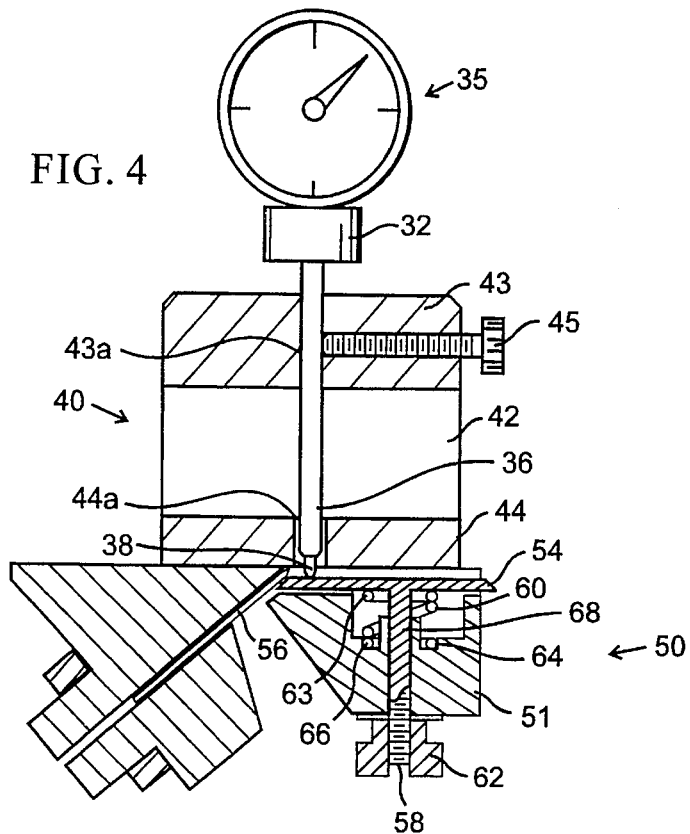
FIG. 4
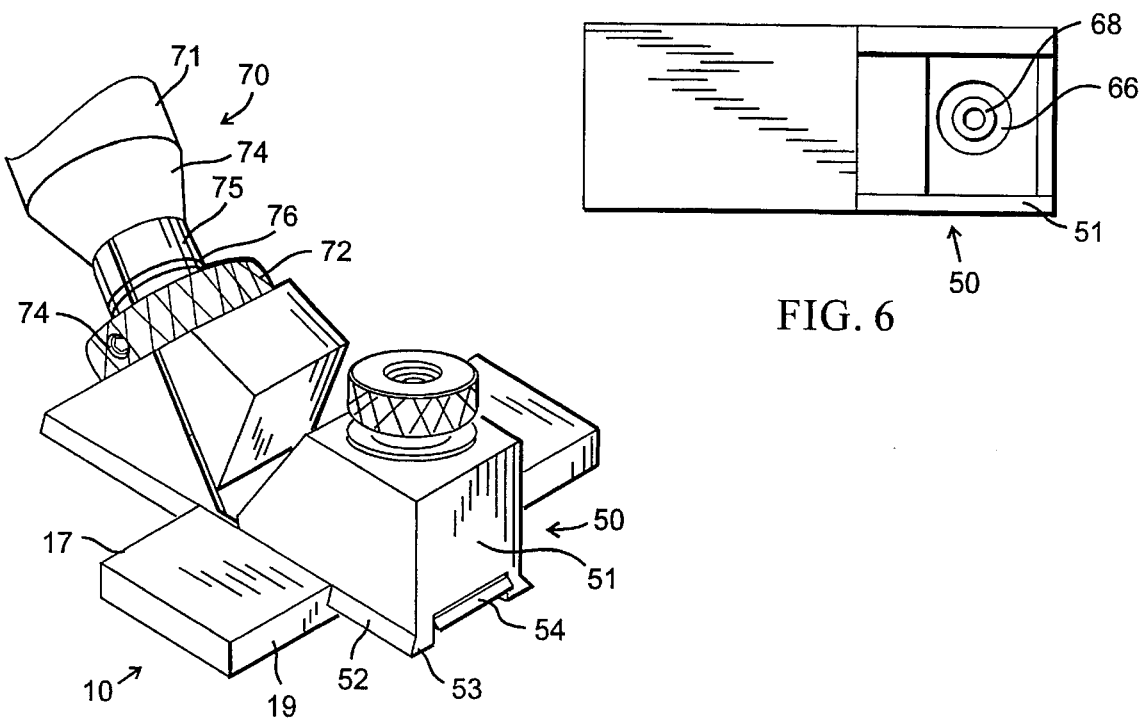
FIG. 6
FIG. 5

KERATOME WITH SPRING LOADED ADJUSTABLE PLATE, CUTTING LENGTH ADJUSTMENT PLATE, METHOD OF CUTTING A CORNEAL FLAP, AND GAUGE-MOUNTED BRACKET FOR ADJUSTING PLATE ON KERATOME HEAD

BACKGROUND OF THE INVENTION

1. Field of the Invention

This invention relates to a keratome with a spring loaded adjustable plate, and a cutting length adjustment plate.

More particularly, the present invention relates to a keratome with a spring loaded adjustable plate that does not wobble or waver, and a cutting length adjustment plate that allows for a pre-cutting measurement of a corneal cut. The present invention also relates to a method of cutting a corneal flap.

In a further and more specific aspects, the invention relates to a gauge-mounted bracket for adjusting the spring loaded adjustable plate on the keratome head.

2. Prior Art

For differing procedures it is required to slice a section from the cornea of the eye. Severe myopia for example, can be corrected by slicing a first hemispherical section from the cornea, e.g, 150 microns, then slicing a second section of perhaps 20–250 microns from the cornea, and reattaching the first section. Less-severe myopia and hyperopia can be corrected by simply slicing a hemispherical section from the cornea, and then reattaching it. The cutting and reattachment of the cornea causes a corneal bulging that can correct vision.

It is known in the art that a keratome is a surgical instrument for making thin slices of the cornea of the eye. The instrument resembles a block plane, however the bottom of the keratome comprises more than one surface. Leading the front end of the keratome is an adjustable plate, followed by the adjustable in length, but fixed in length when used, cutting blade. The keratome blade oscillates at high speed from side to side to better slice the cornea.

The adjustable plate can be moved up or down from the cutting edge of the blade, determining how deep or shallow the corneal cut, respectively. The position of the adjustable plate relative the depth of the blade must be critically set. Yet the adjustable plate itself has a tendency to wobble front to back or waver side to side, and is generally adjusted with a gauge where the keratome is mounted on a stand with a corneal ring. Such conventional measuring means can be cumbersome to use, and can result in imperfect measurements. Additionally, a wobbling or wavering plate can result in a disastrously imperfect corneal cut.

After years of performing these surgeries, it has been noted that the surgery involves one very severe complication; that the first section cut from the cornea may be lost or damaged before reattachment. Therefore it has become common practice for the surgeon to cut a corneal flap, instead of a slice, and then reattach the flap. The flap is cut by moving the keratome over the corneal ring, and alternating between cutting and checking the length of the cut. Sometimes a surgeon will manually hold a rod at a predetermined placement to stop the keratome when it reaches just before where the corneal tissues ends. All too often, a slice is cut instead of the desired flap.

It would be highly advantageous, therefore, to remedy the foregoing and other deficiencies inherent in the prior art.

Accordingly, it is an object of the present invention to provide improvements in a keratome having an adjustable plate.

Another object of the invention is the provision of improvements especially adapted for use in connection with a keratome having an adjustable plate.

And another object of the invention is to provide improved means for stabilizing the adjustable plate of a keratome.

Still another object of the immediate invention is the provision of an improved means for predetermining the length of the corneal cut.

Yet another object of the invention is to provide means for affixing a keratome having an adjustable plate directly to the gauge used to measure plate depth.

Yet still another object of the invention is the provision of improved means for positioning the keratome, and adjusting the blade to cut the cornea at a predetermined length.

A further object of the instant invention is to provide improvements in securing the keratome to a gauge for measuring the depth of the adjustable plate.

SUMMARY OF THE INVENTION

Briefly, to achieve the desired objects of the instant invention in accordance with a preferred embodiment thereof, first provided is a keratome with a spring loaded adjustable plate that include means for restricting the lateral movement of the spring and thereby also restricts the lateral movement of the adjustable plate. This is achieved by the formation of a spring retaining ridge in the keratome where the end of the spring opposite the plate rests, and a cylindrical portion within the ridge, and rising into the interior of the spring. The adjustable plate has beveled side edges so as to fit within a groove across an eye ring, with sides shaped to engage the beveled side edges of the adjustable plate.

Also provided is a cutting length adjustment plate that allows for a pre-cutting setting of the blade to cut the cornea at a particular length. The plate has a width approximately equal to the diameter of an eye ring, and has a groove across its entire width. This groove has sides shaped to engage the beveled side edges of the adjustable plate. The groove also has an elliptical aperture across most of the width of the adjustment plate. Indicia of length appears on the underside of the adjustment plate. When a keratome is engaged to the adjustment plate, the blade is visible through the elliptical aperture, and a nut on the keratome can be adjusted so that it abuts the plate.

In a further aspect, the invention includes a gauge-mounted bracket for adjusting the spring loaded adjustable plate on the keratome. The bracket is a sideways U-shaped member, having a narrow hole in the upper part of the sideways U through which the gauge needle housing is inserted, a wider hole in the lower part of the sideways U through which the gauge needle housing passes freely, a set screw in the upper part of the sideways U for tightening against the gauge needle housing thereby retaining the bracket on the gauge needle housing, and a beveled sided groove on the outer side of the lower part of the sideways U. The keratome is mounted in this beveled groove to hold the keratome in place on the gauge while plate depth is measured with the gauge and its anvil.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIG. 4 is a sectional view along line 4—4 in FIG. 3;

FIG. 5 is a perspective view of the keratome, mounted within the cutting length adjustment plate; and FIG. 6 is a bottom view of the keratome with the spring loaded adjustment plate removed.

PREFERRED EMBODIMENT OF THE PRESENT INVENTION

Figure 1:
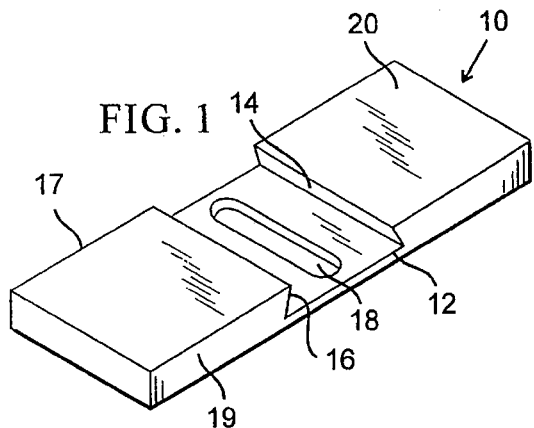
FIG. 1 is a perspective view of the cutting length adjustment plate.

Turning now to the drawings in which like reference characters indicate corresponding elements throughout the several views. Attention is first directed to FIG. 1, wherein cutting length adjustment plate 10 is shown.

As shown plate 10 is generally a long, narrow and thin box; it is generally rectangular with a narrow thickness. It should be apparent though that plate 10 could be many different shapes.

Plate 10 houses groove 12 in top surface 20, and has front surface 19 and rear surface 17, which is analogous to front 19. Groove 12 has beveled sides 14 and 16, and aperture 18, and is adapted for mounting a keratome within groove 12. Groove 12 is also approximately equal in length to the groove in a conventional eye ring.

Figure 2:
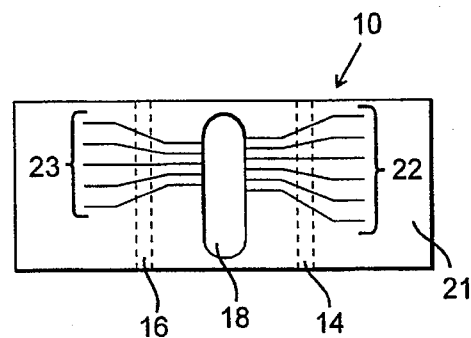
FIG. 2 is a lower view of the cutting length adjustment plate.

FIG. 2 shows plate 10 from plate bottom 21. Bottom 21 is on the opposite side of plate 10 from groove 12. Markings 22 and 23 on plate bottom 21 are calibrated with indicia, generally ranging from 4.5 to 7.5 (not shown), and corresponding to the size of the flap of cornea to be cut. Generally, a cut of 4.5 to 6.5 is needed for hyperopia patients, and a cut of 7.2 is needed for myopia patients.

A user would slide a keratome into groove 12 until the leading edge of the keratome blade lined up with the indicia indicating the desired size of the flap of cornea to be cut. Then the user would adjust stop nut 72 (FIG. 5) so that the lower edge of the front of stop nut 72 is even with plate rear 17, and lock stop nut 72 in place with lock screw 74. Then when the keratome is run across the eye ring through the eye ring groove, stop nut 72 engages the end of eye ring ensuring the cut is the same length as was measured above.

Figure 3:
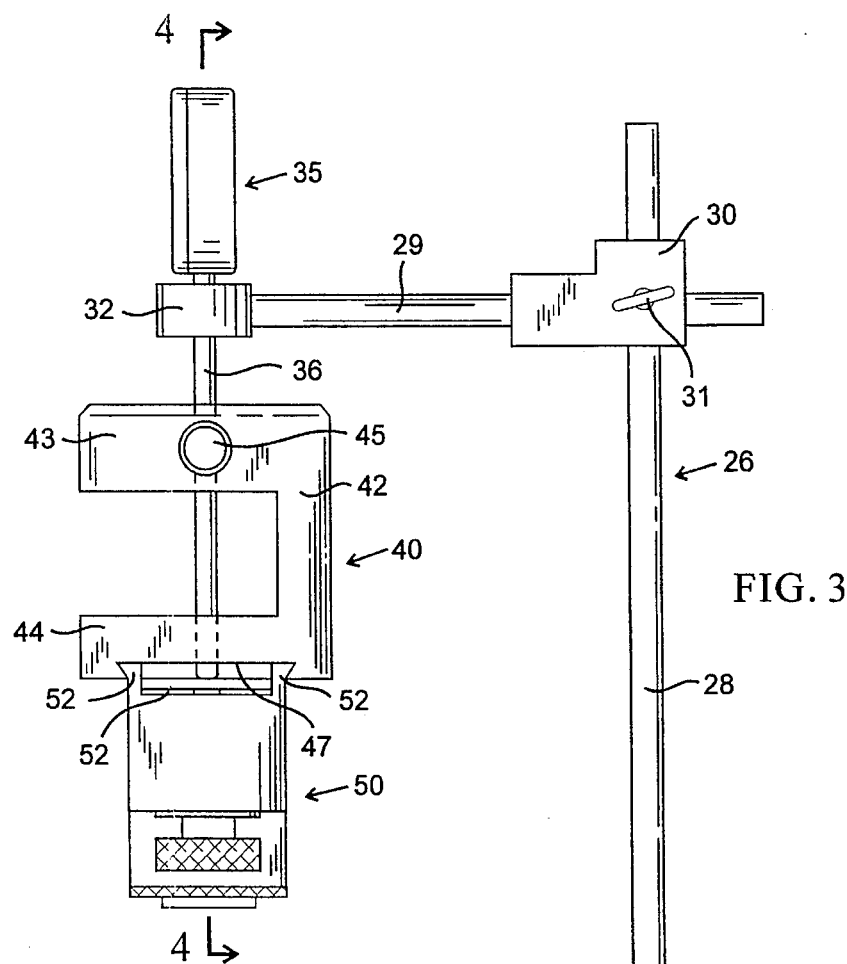
FIG. 3 is a side view of a stand with gauge for measuring the plate depth, showing the gauge-mounted bracket for adjusting the spring loaded adjustable plate on the keratome.

Turning to FIG. 3, shown from the right side is a plate depth gauge 35 mounted on gauge stand 26. Stand 26 has base 27, vertical rod 28, horizontal rod 29, right angle bracket 30, which holds rods 28 and 29 perpendicular to each other, and butterfly set screw 31. Screw 31 runs through a hole (not shown) in rod 29 to hold rod 29 along the height of rod 28. A few other holes (not shown) along the length of rod 29 allow rod 29 to be extended or withdrawn against rod 28. Likewise loosening screw 31 allows bracket 30 and rod 29 to be moved, and then fixed by a tightening of screw 31, up and down along rod 28.

Gauge 35 has anvil shroud 36. Within shroud 36 is anvil 38 (FIG. 4). The gauge assembly is retained in stand 26 by inserting shroud 36 through a hole in stand ring 32, mounted at the end of rod 29, until the lower part of gauge 35 rests against ring 32.

Gauge-mounted bracket 40 has vertical portion 42, upper horizontal portion 43, and lower horizontal portion 44. Upper horizontal portion 43 and lower horizontal portion 44 each have a vertical hole in their centers (not shown) through which shroud 36 goes. Knurled knob screw 45 tightens bracket 40 against shroud 36, and holds bracket 40 on shroud 36.

Bracket 40 has groove 47 at the bottom of lower horizontal portion 44. Groove 47 is shaped so as to enable keratome 50 with flairs 52 to be slidably engaged. Bracket 40 enables keratome 50 to be quickly and easily engaged relative gauge 35 for adjusting spring loaded adjustable plate 54 on keratome 50.

FIG. 4 details a frontal view of most of the apparatus in FIG. 3, but is a sectional view taken along line 4—4 in FIG. 3. This figure affords a better view of knurled knob screw 45, and holes 43a and 44a in upper and lower horizontal portions 43 and 44, respectively.

In operation, first gauge 35 is "zeroed" by placing anvil 38 against the tip of blade 56 and then set to zero with its zeroing adjustment knob (not shown). Then keratome 50 is slid relative bracket 40 so that anvil 38 rests against plate 54. The reading on gauge 35 will be the plate depth.

Spring loaded adjustable plate 54 is mounted to post 58 which is threaded at least at its end. Spring 60 is mounted about post 58, and when knurled round nut 62 is engaged with post 58, holds plate 54 outward relative keratome head 51.

Spring end 63 rests against plate 54. The other end of the spring, end 64, rests within circular groove 66 formed in keratome head 51. This prevents spring end 64 from moving against head 51, and thereby causing plate 54 to go askew.

Additionally head 51 has collar 68. Spring 60 surrounds collar 68 and is thereby prevented from side to side flexing, which would also cause plate 54 to go askew. FIG. 6 is a view of keratome 50 from its bottom, with plate 54 and its attached post 58, and spring 60 removed. This view clearly shows circular groove 66 and collar 68.

FIG. 5 shows keratome 50 mounted in plate 10. Keratome 50 fits in sliding engagement with plate 10, as it does with bracket 40.

Keratome handle 70 is threadedly engaged to keratome 50. Handle 70, generally formed as one piece, has grip portion 71, frusto-conical narrowing portion 74, and sleeve 75, and threads 76 on the outside of sleeve 75 for engaging handle 70 to keratome 50. In this embodiment of handle 70 threads 76 are extended to appear much higher than usual along sleeve 75. Riding on threads 76 of sleeve 75 is stop nut 72, having lock screw 74. To adjust the blade to its desired cutting length, the blade of keratome 50 must be aligned with plate indicia 22 or 23. Stop nut 72 may be adjusted inwardly or outwardly along sleeve 75 so that its lower edge is even with plate rear 17. Then stop nut 72 may be locked in place with lock screw 74. It must be noted however that while in this embodiment, sleeve 75, stop nut 72, and lock screw 74, are part of keratome handle 70, they could also be part of the structure of keratome 50.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A keratome adjustment plate for measuring a desired length cut of cornea, comprising:

a plate having top and bottom surfaces and first and second side edges, said top surface with a transverse groove sized for sliding engagement with a keratome;

an aperture parallel to and within said groove for viewing a tip of a blade of said keratome; and indicia on the bottom surface of said plate to measure the distance the tip of said blade travels within said plate from one of said side edges of said plate to said indicia.

2. The adjustment plate of claim 1 wherein said indicia ranges from 4.5 to 7.5 mm.

3. A keratome having a spring loaded plate wherein:

said keratome has a head;

said spring loaded plate is mounted to said head via a post inserted through a hole in said head, said post having one end connected to said plate, and threaded at the other end; and said head has a collar formed on said head to ride within a spring.

4. The keratome of claim 3 further comprising a groove in said keratome head, said groove to hold a free end of said spring.

5. The keratome of claim 4 wherein said groove and said collar are circular.

6. The keratome of claim 5 wherein said groove and said collar are concentric.

* * * * *